United States Patent [19]
Cicierega et al.

[11] Patent Number: 6,005,018
[45] Date of Patent: *Dec. 21, 1999

[54] AUGMENTATION DEVICE FOR JOINT PROSTHESIS

[75] Inventors: Gerald J. Cicierega, Bridgewater; Robert C. Hurlburt, Whitman; Michael J. O'Neil, West Barnstable, all of Mass.

[73] Assignee: Johnson & Johnson Professional, Inc., Raynham, Mass.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/741,581

[22] Filed: Nov. 1, 1996

Related U.S. Application Data

[63] Continuation of application No. 08/456,476, Jun. 1, 1995, abandoned.

[51] Int. Cl.$^6$ .................................................. A61F 2/38
[52] U.S. Cl. ................................................ 523/20; 623/18
[58] Field of Search ................................ 623/18, 20, 19; 606/53, 57, 59, 63, 65, 67, 70–72; 411/55, 60

[56] References Cited

U.S. PATENT DOCUMENTS

| | | |
|---|---|---|
| 1,664,566 | 4/1928 | Marshall . |
| 1,816,970 | 8/1931 | Hess ........................... 411/60 |
| 2,490,364 | 12/1949 | Livingston ................... 606/68 |
| 2,616,328 | 11/1952 | Kingsmore ................... 411/60 |
| 3,076,453 | 2/1963 | Tronzo ........................ 606/67 |
| 4,312,614 | 1/1982 | Palmer et al. ............... 411/44 |
| 4,711,232 | 12/1987 | Fisher et al. ............... 606/67 |
| 4,769,039 | 9/1988 | Horber ........................ 623/20 |
| 4,878,791 | 11/1989 | Kurihara et al. ............ 411/55 |
| 4,952,106 | 8/1990 | Kubogochi et al. .......... 411/48 |
| 4,971,500 | 11/1990 | Benoit et al. ............... 411/55 |
| 4,995,883 | 2/1991 | Demane et al. .............. 623/23 |
| 5,039,267 | 8/1991 | Wollar ........................ 411/508 |
| 5,080,674 | 1/1992 | Jacobs e tal. ............... 623/20 |
| 5,108,446 | 4/1992 | Wagner et al. .............. 623/18 |
| 5,226,915 | 7/1993 | Bertin ......................... 623/20 |
| 5,268,001 | 12/1993 | Nicholson et al. .......... 606/72 |
| 5,549,685 | 8/1996 | Hayes ......................... 623/20 |

FOREIGN PATENT DOCUMENTS

| | | |
|---|---|---|
| 0433121B1 | 11/1990 | European Pat. Off. . |
| 0634154A1 | 7/1994 | European Pat. Off. . |
| 2223174 | 4/1990 | United Kingdom ........ 623/20 |
| 2266246 | 3/1993 | United Kingdom . |

*Primary Examiner*—Bruce E. Snow

[57] ABSTRACT

An augmentation system for an implantable bone prosthesis, such as a femoral component of a knee joint prosthesis, includes an augmenting block having an aperture disposed therein. A collet having an expandable distal end, extending beyond one surface of the augmenting block, is positioned within the aperture. The proximal end of the collet includes a threaded cavity that receives a set screw which is adapted to communicate with the collet to expand and contract the collet. The distal end of the collet is adapted to fit within a mounting cavity of a joint prosthesis. With the augmenting block placed on the appropriate surface of the joint prosthesis, the distal end of the collet is positioned within the mounting cavity. Tightening of the set screw causes the distal end of the collet to expand, thus frictionally and/or mechanically engaging the interior walls of the mounting cavity to firmly secure the augmenting system to the prosthesis.

11 Claims, 5 Drawing Sheets

AUGMENTATION DEVICE FOR JOINT PROSTHESIS

This application is a Continuation Application under 37 C.F.R. 1.62 of prior application Ser. No. 08/456,476 filed on Jun. 1, 1995, now abandoned, entitled: AUGMENTATION DEVICE FOR JOINT PROSTHESIS.

BACKGROUND OF THE INVENTION

This invention relates to devices useful to augment bone deficiencies encountered during joint arthroplasty procedures.

Joint arthroplasty is a well known surgical procedure by which a diseased and/or natural joint is replaced by a prosthetic joint. Joint arthroplasty is commonly performed for knees, hips, elbows, and other joints. In some instances, due to disease or trauma, insufficient healthy boney mass exists at the distal end of a bone to which a joint prosthesis is to be secured. In arthroplasty procedures, it is often necessary to remove a portion of bone (such as a portion of the femur) to ensure sufficient anchoring and a proper fit for a prosthesis. In the example of knee joint arthroplasty, it is necessary to augment the inferior portion of the femoral component of the prosthesis to add additional thickness to the prosthesis to compensate for the lack of sufficient boney tissue.

Augmentation of the boney mass can be accomplished by securing augmenting devices to a component of the joint prosthesis, such as a femoral component. Some earlier devices used to augment knee femoral components must be cemented to the inferior surface of the femoral component. The techniques used to install such devices require accurate measurements and a great deal of precision since the augmenting device is difficult, if not impossible, to remove once it is secured to the prosthesis. These techniques also tend to be rather time consuming.

An improved augmentation device is described in U.S. Pat. No. 4,936,847 (Manginelli). This patent discloses an augmentation system that can be removeably and replaceably secured within a femoral component of a knee joint prosthesis. Such a design is advantageous because it avoids the need to cement augmenting devices to the inferior surface of the femoral component. As a result, augmenting devices of varying thicknesses can be fitted into place on the inferior surface of the femoral component. The augmenting devices can be removed and replaced with devices having different dimensions until the proper augmentation thickness is determined. Such an augmentation system, however, requires a specially constructed femoral component.

Despite existing augmentation systems, there remains a need to provide improved systems that allow standard augmenting components to be easily and securely affixed within a prosthesis component. The cost of joint prostheses that utilize many current augmentation systems can be quite high because the tight tolerances required often result in a high scrap rate. There is thus a need for an augmentation system that allows augmenting devices to be easily and securely fitted to prosthesis components.

It is thus an object of the invention to provide a prosthesis augmentation system that securely and easily fits within a component of a joint prosthesis. A further object is to provide an augmentation system that offers more cost effective manufacturing potential as well as a reduced part rejection rate. Another object is to provide an augmentation system that is well suited for use with femoral components of knee joint prostheses. It is also an object to provide an augmentation system that offers a great deal of versatility in that it can be used with different types of femoral components, including cruciate retaining and cruciate sacrificing femoral components. A further object is to provide an augmentation system that can be used in a prosthesis component without the need for post-casting modification of the prosthesis. Other objects will be apparent to those of ordinary skill in the art upon reading the description that follows.

SUMMARY OF THE INVENTION

The present invention relates to an augmentation system for use with joint prostheses. The system of the present invention serves to provide increased thickness to prosthesis components where boney deficiencies exist in the bones of a patient to which the prosthesis is to be secured. The augmentation system of the invention is particularly well suited for use in augmenting a femoral component of a knee prosthesis.

The augmentation system of the invention includes an augmenting block having first and second surfaces, which in one embodiment may correspond to distal and proximal surfaces, respectively. An aperture is formed in the augmenting block and extends between the first and second surfaces of the augmenting block. An expansion collet is secured within the aperture such that a stem at a distal end of the collet extends beyond the first surface of the augmenting block. An internal cavity is formed within at least a proximal portion of the collet and a set screw is adapted to seat within this cavity. The set screw cooperates with the collet such that sufficient tightening of the screw within the collet facilitates the expansion of the outer diameter of the distal stem portion of the collet. Conversely, loosening of the set screw decreases the diameter of the stem of the collet.

The augmenting block can be of a variety of shapes and dimensions suitable to be disposed at various desired locations within an implantable prosthesis, such as a femoral component of a knee joint prosthesis. For example, the augmenting block can be disposed on the inferior surfaces of an artificial knee joint femoral component, including on the posterior chamfer, the posterior flange of the condyle (medial or lateral side), or at the inferior surface of a condyle (lateral or medial side).

Preferably, the augmenting block is secured to a joint prosthesis component, in a desired location, by positioning the distal stem of the collet within a mounting cavity formed in the joint prosthesis. Once the augmenting block is properly positioned and aligned, the set screw is tightened thereby expanding the diameter of the distal stem of the collet to the extent that it engages the inner walls of the cavity. Sufficient tightening of the set screw causes expansion of the distal stem of the collet and results in secure placement of the augmenting block on the prosthesis such that the collet grabs the cavity of the prosthesis with a pulling axial load. Among the noteworthy advantages of this augmentation system are the reduced assembly time during surgical procedures and the tight securement of the augmenting block to the prosthesis.

DETAILED DESCRIPTION OF THE INVENTION

Figure 1:
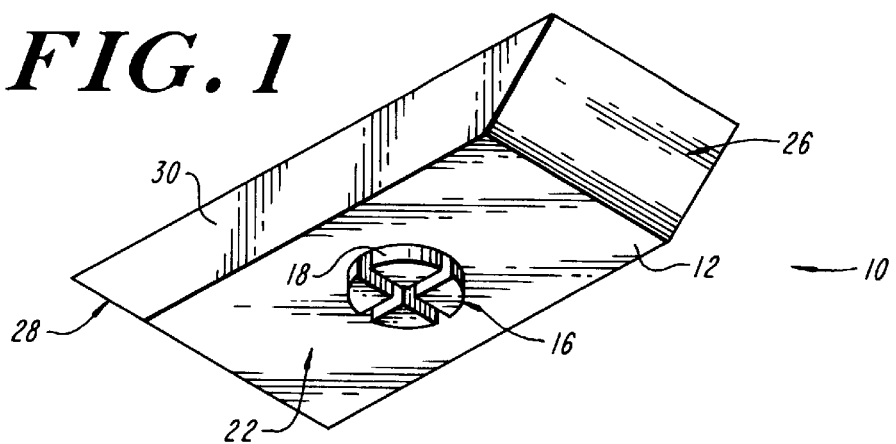
FIG. 1 is perspective view of an augmentation system constructed according to the present invention.
Figure 2:
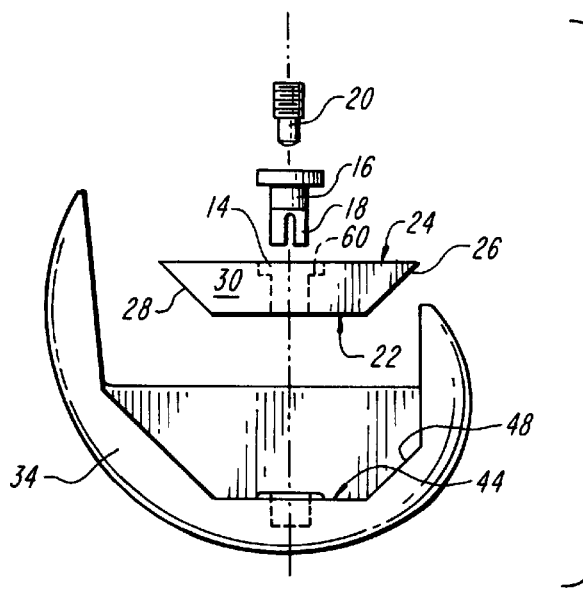
FIG. 2 is an exploded view of an augmentation system constructed according to the present invention, illustrating a femoral component of a knee prosthesis, an augmenting block, an expandable collet, and a set screw.
Figure 3:
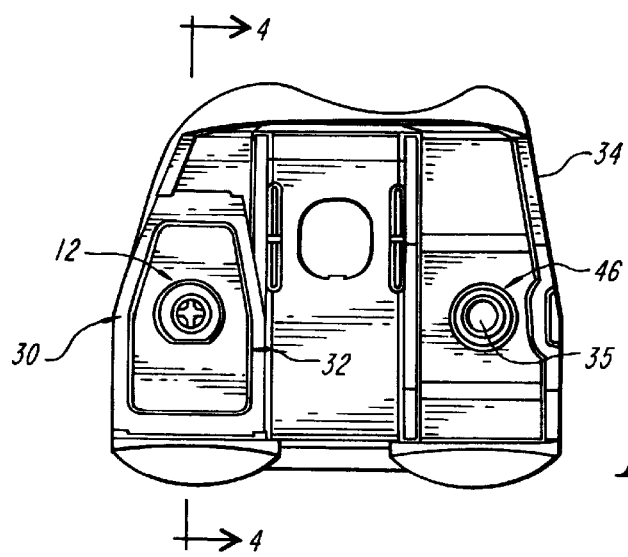
FIG. 3 is a top view of the augmentation system illustrated in FIG. 1, mounted within a knee femoral component.

As illustrated in FIGS. 1 through 5, the augmentation system 10 includes an augmenting block 12 having extending therethrough an aperture 14 which is substantially centrally located. Augmentation system 10 further includes an expandable collet 16 that is disposed within aperture 14 and a set screw 20 which is disposed within an internal, threaded cavity 17 at a proximal portion of the collet.

By way of example, the present augmentation system is described with reference to an anticipated use in augmenting a femoral component of a knee joint prosthesis. It is understood, however, that this augmentation system may be adapted for use in a variety of joint prostheses. A particular advantage of the present augmentation system, which lends itself to use with various types of joint prostheses, is the ease with which it is secured to a prosthesis. Moreover, this augmentation system is able to be firmly secured to a prosthesis, with little or no relative movement between the augmentation components and the prosthesis. The prosthesis further does not require post-casting machining processes to accept the augmentation system. One of ordinary skill in the art will be able to alter the shape and dimensions of the augmentation system described herein to fit other prostheses.

The augmentation block 12 illustrated in FIGS. 1 through 5 is adapted to mount on either the medial or lateral inferior condylar surfaces 44, 46 of a femoral component 34 of an artificial knee joint. Block 12 may be adapted for use in either left or right side knee prostheses. An augmenting block suitable for a left side prosthesis can mount upon either the medial or lateral inferior condylar surfaces 44, 46 thereof, and an augmenting block suitable for a right side prosthesis can mount upon either the medial or lateral inferior condylar surfaces of the prosthesis. As illustrated, block 12 has a first (distal) surface 22 and a second (proximal) surface 24. The area of the proximal surface 24 preferably is greater than the area of the distal surface 22 in order for the block to conform to the geometry of the inner condylar surface of a knee joint femoral component.

Figure 4:
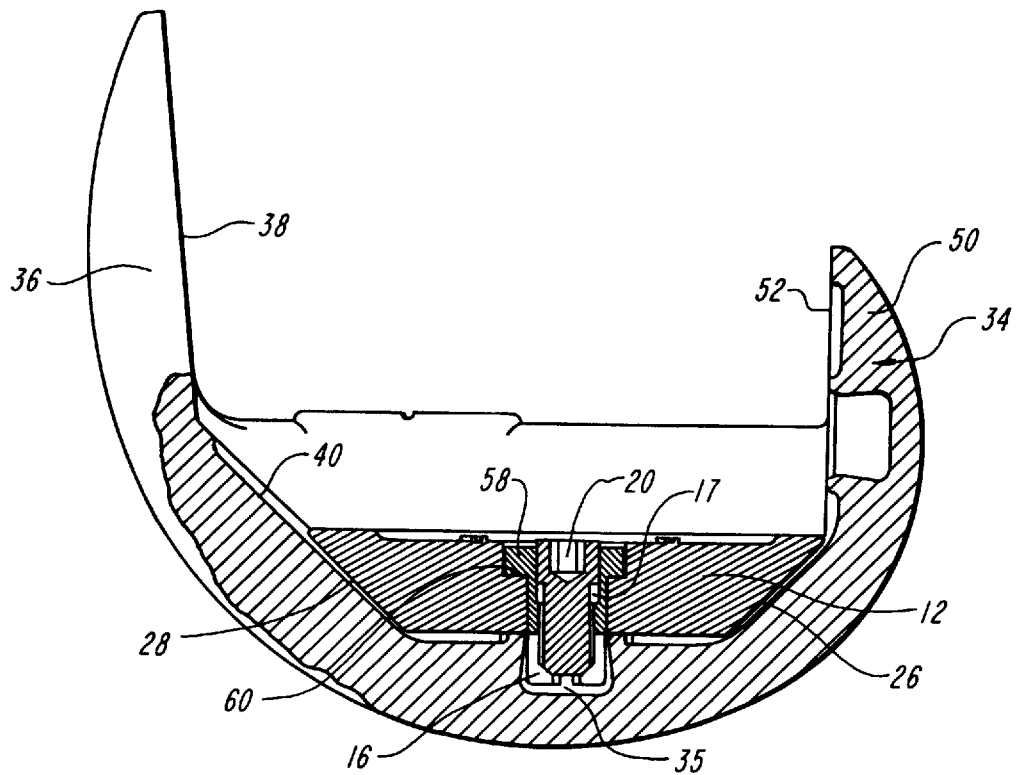
FIG. 4 is a sectional view, at lines 4—4, of an augmentation system of FIG. 3.
Figure 5:
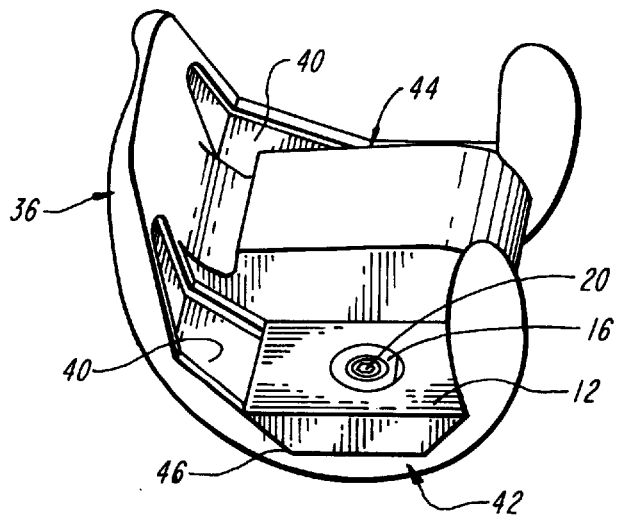
FIG. 5 is a perspective view of the augmentation system of the type shown in FIG. 1 disposed on the inferior surface of a medial condyle of the femoral component of a knee joint prosthesis.

Augmenting block 12 has two opposed, canted surfaces 26, 28 that can be either posterior or anterior surfaces, depending upon whether the augmentation block is mounted on the medial or lateral sides, or on a left or right side prosthesis. Preferably, surfaces 26, 28 are canted such that each surface slopes inwardly from the proximal surface 24 to the distal surface 22 as shown in FIG. 4. The angle of the canted surfaces 26, 28 can vary as will be appreciated by those having ordinary skill in the art. As shown in FIG. 5, the angle of surfaces 26, 28 corresponds to the angle of the anterior and posterior chamfers 40, 48 of a femoral component 34 to enable proper seating of the augmenting block 12 within a femoral component.

Augmenting block 12 further includes surfaces 30, 32 which correspond to either medial or lateral facing surfaces, depending upon whether the augmentation block 10 is used on the lateral or medial sides of a prosthesis, or in a left or right side prosthesis. Side surfaces 30, 32 preferably are substantially vertical and extend at a right angle with the plane of the proximal or distal surfaces 24, 22.

Figure 6A:
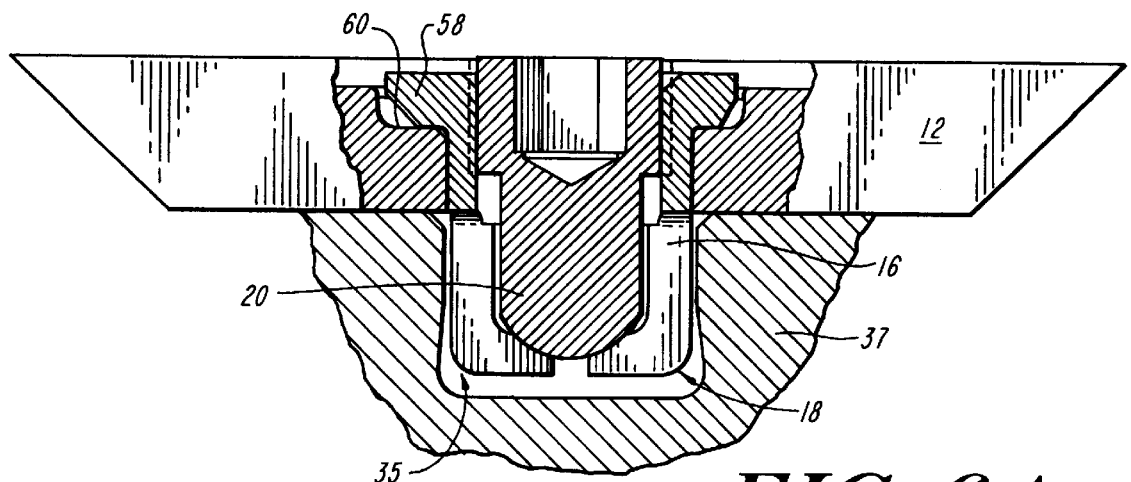
FIG. 6A is a partial sectional view showing engagement of the augmentation system of the invention with a prosthesis with the collet stem in a non-expanded condition.
Figure 6B:
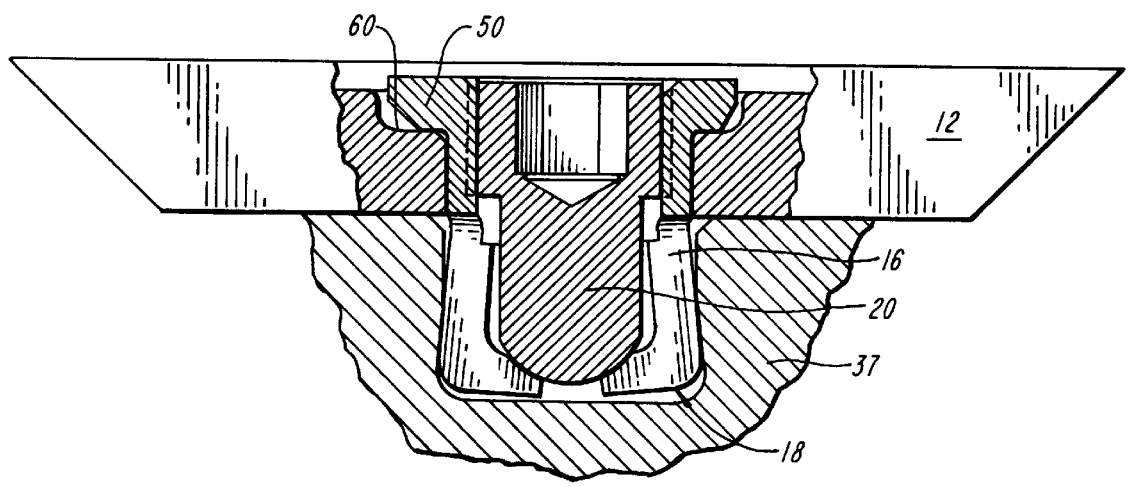
FIG. 6B is a partial sectional view illustrating the engagement of the augmentation system of the invention with the prosthesis with the collet stem in the expanded condition.

As illustrated in FIGS. 5, 6A and 6B, augmentation block 12 is adapted to mount on a prosthesis component, such as the inferior surface of the lateral or medial condyles 44, 46, such that the distal surface 22 of block 12 contacts the inferior surface of femoral component 34. The distal stem 18 of collet 16 preferably extends beyond the distal surface of block 12 by a distance sufficient to enable distal stem 18 of collet 16 to fit within a mounting cavity 35 disposed in a surface of the femoral component to be augmented. The frictional and/or mechanical engagement of the distal stem 18 of collet 16 enables the augmentation system 10 to be secured to an appropriate surface of the femoral component. The distance by which distal stem 18 extends beyond distal surface 22 of block 12 will vary depending upon the requirements of a given application. Typically, this distance is about 0.155 to 0.175 inches, and most preferably about 0.165 inches. The length of the distal stem 18 should not be so great that its distal end contacts the bottom of cavity 35.

As noted above, set screw 20 controls the expansion and contraction of the distal stem 18 of collet 16. Tightening the set screw expands the distal stem 18, while loosening screw 20 enables a once expanded distal stem 18 to contract. FIG. 6A illustrates the mounting of augmentation block 12 to a prosthesis component 37 while distal stem 18 of collet 16 is in a non-expanded condition. When stem 18 is in the non-expanded condition, there is little or no frictional and/or mechanical engagement between stem 16 and mounting cavity 35; the augmentation block 12 can be freely removed and inserted into mounting cavity 35 in this condition. FIG. 6B illustrates the mounting of augmentation block 12 upon a prosthesis component 37 when the stem 18 is in the expanded condition. In this condition, sufficient frictional and/or mechanical engagement exists between the stem 18 and the walls of the mounting cavity 35 to enable the augmentation block to be held firmly on the prosthesis component.

Figure 10A:
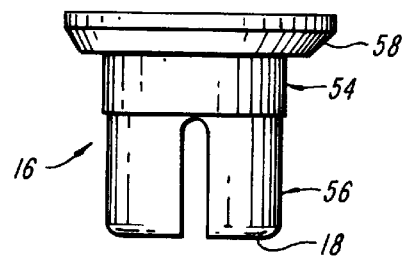
FIG. 10A is a side view of an expandable collet useful with the present invention.
Figure 10B:
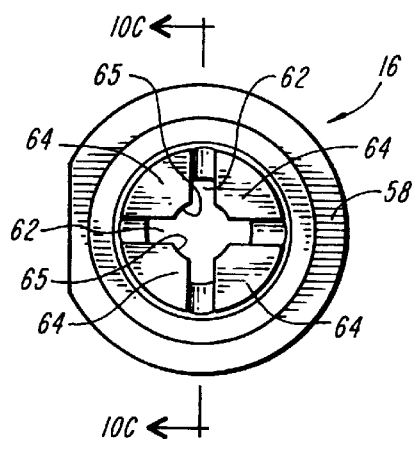
FIG. 10B is a bottom view of the collet shown in FIG. 10A.
Figure 10C:
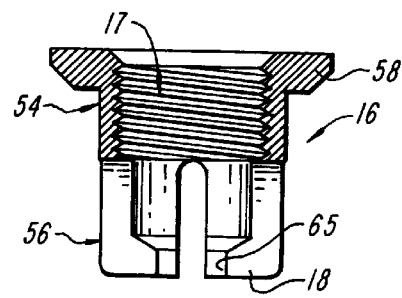
FIG. 10C is a cross-sectional view, at lines 10C—10C, of the collet shown in FIG. 10B.

Collet 16, as illustrated in FIGS. 10A, 10B, and 10C, includes a proximal region 54 and a distal region 56. Proximal region 54 includes a collar 58, which can mount within a recessed area 60 in the proximal surface of augmenting block 12, as shown in FIGS. 4, 6A and 6B. The collar 58 and recessed area 60 can be of virtually any corresponding shapes, including for example, circular and D-shaped. A D-shaped collar, or another irregularly shaped collar, can be useful to prevent unwanted rotation of the collet within aperture 14.

The distal stem 18 of collet 16 preferably is slotted, with two perpendicular slots 62 extending therein. Preferably, the slots 62 separate the stem into four substantially triangular shaped wedges 64, when viewed from the bottom as shown in FIG. 10B. FIG. 10C illustrates that the interior portion of distal stem 18 is angled inwardly to the tip 65 of wedges 64. This configuration enables the internal geometry of the distal stem 18 to cooperate with a radius tip 66 at a distal end of screw 20, as shown in FIG. 11, to cause the distal stem 18 of collet 16 to expand and the wedges 64 to separate when distal end 74 of the screw 20 is forced into engagement with the corresponding internal surfaces of wedges 64.

Figure 11:
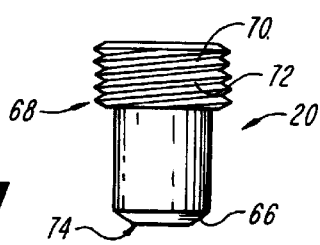
FIG. 11 is a side view of a set screw useful with the augmentation system of the present invention.

As illustrated in FIG. 11, screw 20 also includes a proximal end 68 having a head portion 70. The head further includes a threaded region 72 that engages an internally threaded region of the collet 16. A distal end 74 of screw 20 preferably has a geometry that will cause expansion of the distal stem of the collet. The distal end 74 of the screw can include a radius tip point 66, a dogged end (not shown), or similar geometries. Preferably, the head 70 of screw is a hex head.

The dimensions of the aperture 14 in the augmentation block 12, the collet 16, and the mounting cavity 35 of the femoral component can vary as will be understood by one of ordinary skill in the art. It is essential, however, that the relative dimensions of the components be such that the collet 16 have a relatively tight frictional fit within aperture 14, and that rotation of the collet within aperture 14 be prevented. In a preferred embodiment the collet 16 has a diameter slightly greater than the diameter of the aperture 14. Thus, the collet 16 is press fit within aperture 14 to prevent rotation and separation. Preferably the size differential ranges from about 0 to 0.002 inch.

Further, the non-expanded stem 18 should fit within the mounting cavity 35 without excessive friction. The expanded stem 18 should firmly engage the inner walls of mounting cavity 35 to prevent dislodgment or movement of the augmentation block 12. The dimensions of these components will vary depending upon the requirements of a given application, however one of ordinary skill in the art can readily determine the desired dimensions. Generally, the diameter of the distal stem 18 of the collet 16 in the non-expanded condition is approximately 0.240 to 0.260 inch, and preferably about 0.250 inch. The diameter of the distal stem 18 of collet 16 in the expanded condition preferably is about 0.010 to 0.020 inch greater than the diameter in the non-expanded condition. The diameter of the mounting cavity 35 is sufficient to yield a secure interference fit between the collet stem and the cavity when the collet stem is expanded. Preferably, the mounting cavity has a diameter of about 0.26 inch, ±0.10 inch. The depth of mounting cavity 35 can vary, as will be understood by those having ordinary skill in the art, but preferably the depth is about 0.18 to 0.206 inch. As noted above, the distal stem 18 of collet 16 should not bottom out within cavity 35.

The collet and screw can also be of dimensions that are readily ascertainable to one of ordinary skill in the art.

Preferably, the collet has a length of approximately 0.25 to 0.60 inch and the stem has a length of approximately 0.16 to 0.18 inch. These dimensions obviously will vary depending upon the size and shape of the prosthesis to be augmented.

Figure 7:
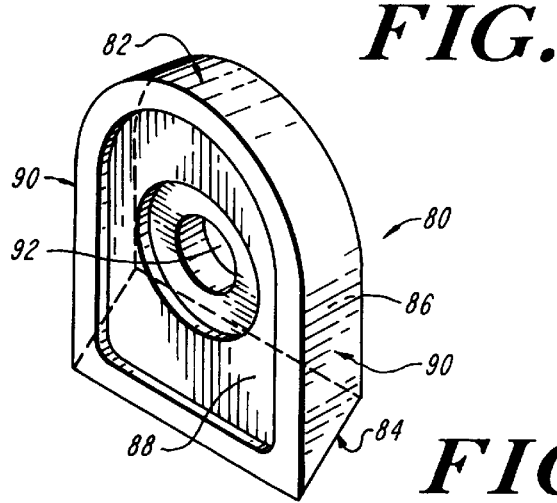
FIG. 7 is a perspective view of an augmentation system of the present invention adapted to fit a femoral component of a knee joint prosthesis at the inferior surface of the posterior flange thereof.
Figure 8:
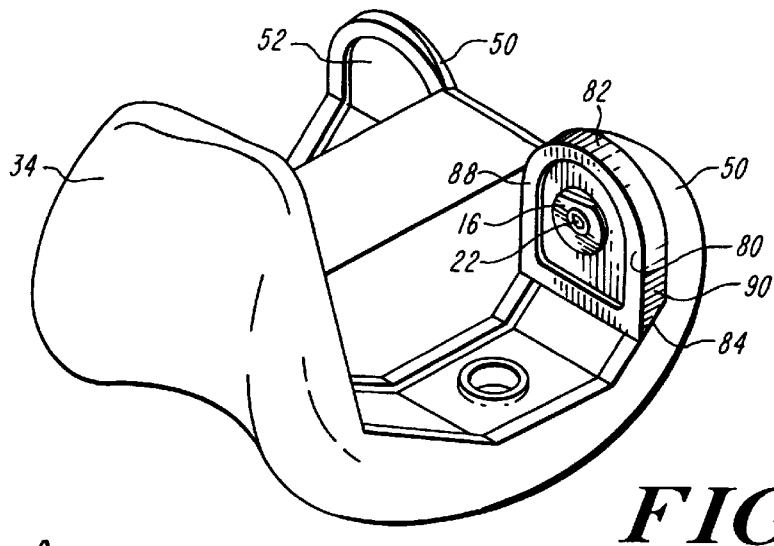
FIG. 8 is a perspective view illustrating the augmentation system of FIG. 7 mounted to a knee joint prosthesis.
Figure 9:
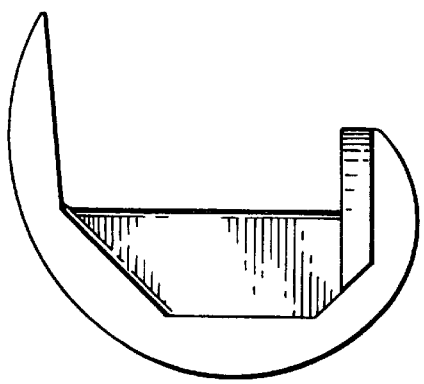
FIG. 9 is a side view of the augmentation system illustrated in FIG. 8.

FIGS. 7 through 9 illustrate one example of an alternative augmenting block 80 that is useful for augmenting another area of a knee femoral component. Augmenting block 80, is constructed to be suitable for mounting on the inferior surface 52 of either the lateral or medial posterior flanges 50. As illustrated, augmenting block 80 includes a convex or dome-like proximal surface 82 and a distal surface 84 that is canted in order to seat on the posterior chamfer 48 of femoral component 34. Anterior surface 86 of block 80 is non-canted and is adapted to mount against the inferior surface 52 of the lateral or medial posterior flange 50 of femoral component 34. Posterior surface 88 of block 80 is likewise non-canted and extends in a plane that is parallel to the plane of anterior surface 86. Lateral and medial sides 90 are also non-canted and are oriented perpendicularly to surfaces 86 and 88. Aperture 92 extends from the posterior surface 88 to the anterior surface 86 and is adapted to seat collet 16 in the manner described above with respect to FIGS. 1 through 6B. The distal stem 18 of the collet 16 extends beyond the anterior surface of block 80, and is adapted to seat within a mounting cavity 35 disposed in the inferior surface 52 of lateral or medial posterior flange 50.

Figure 12A:
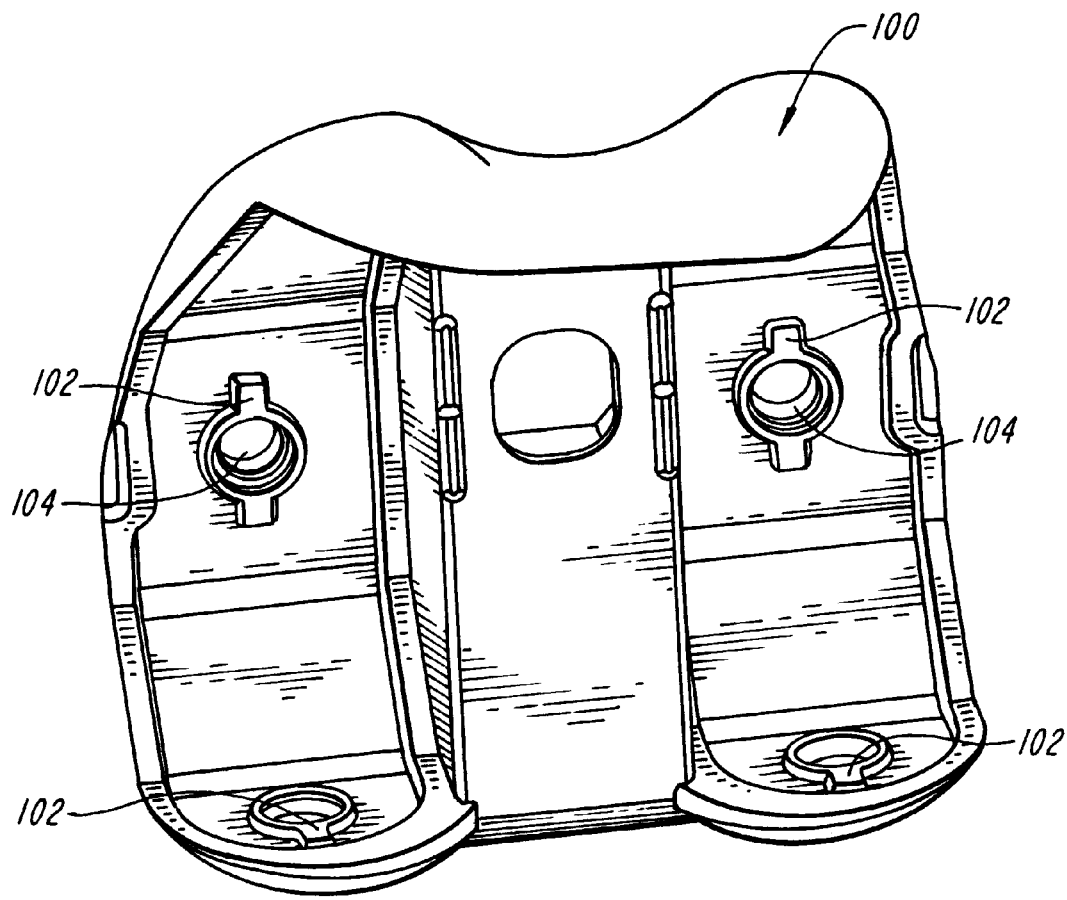
FIG. 12A is a top view (of the inferior surface) of a femoral component useful in connection with the present invention.
Figure 12B:
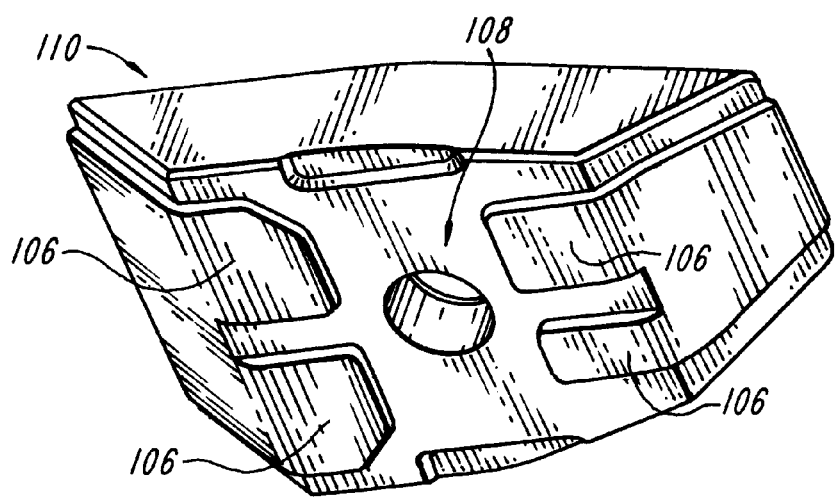
FIG. 12B is a perspective view, illustrating the distal surface, of an augmenting block according to the present invention.

As shown in FIGS. 12A and 12B, the augmentation system of the invention may be configured to include surface features that serve to prevent rotation of an augmenting block once it has been mounted upon a prosthesis. Knee femoral component 100 includes raised femoral surface features 102 surrounding and adjacent mounting cavities 104. The raised femoral surface features cooperate with raised surface features 106 an the distal surface 108 of augmenting block 110. Although these surface features are described only with respect to an augmenting block that mounts upon the inferior condylar surface of a knee femoral, it is understood that surface features may be used with augmenting systems that mount in other regions of a knee femoral, and with augmenting systems that mount in other prostheses. Further, one of ordinary skill in the art can easily vary the shape and dimensions of such surface features.

The dimensions of the augmentation system of the invention can vary as required by the dimensions of the joint prosthesis with which the system is to be used and the amount of augmentation that is required. One of ordinary skill in the art will be able to determine the proper dimensions of the augmentation system 10 of the present invention so as to closely fit the configuration of the inferior surfaces of a joint prosthesis (such as a femoral component) with which the augmentation system is to be used. Generally, the thickness (proximal to distal for augmenting block 12, anterior to posterior for augmenting block 80) of the augmentation system is in the range of about 2 to 20 mm while the width of the augmentation system (medial to lateral) ranges from about 10 mm to 40 mm, and the length (anterior to posterior for augmenting block 12, or proximal to distal for augmenting block 80) ranges from about 10 mm to 60 mm.

The augmentation system of the invention can be made from a variety of biocompatible materials having high strength, durability and resistance to wear debris. Examples of such materials include metal alloys such as cobalt chromium alloy, titanium vanadium alloy, stainless steel, ceramics and other materials, including polymers, that are well known for use in the manufacture of implantable bone prostheses.

A preferred material for the augmentation system, as well as for many prostheses, is a cobalt chromium alloy such as ASTM F-75.

The collet components preferably are made from a malleable metal or metal alloy to reduce the risk of tensile failure as a result of collet expansion. Such materials should be able to deform (but not fail) when subjected to a torque of about 20 to 65 in-lbs, and more preferably about 25–35 in-lbs. A preferred material is a wrought cobalt chromium alloy such as ASTM F-90.

The set screw preferably is made from a metal or metal alloy that has a higher modulus and a greater hardness than does the collet. This ensures that the collet will deform (and not the set screw) when subjected to torque by the screw. A preferred material from which the set screws can be manufactured is wrought cobalt chromium alloy such as ASTM F-799.

The augmentation system of the invention offers many advantages. For example, the augmentation system is able to be secured to a joint prosthesis (such as a knee femoral component) without bone cement, in a secure fit, with improved tensile securement values, such that relative motion between the joint prosthesis and the augmentation system is relatively low or nonexistent. The tensile securement values preferably are in the range of about 50 to 500 kg. This secure fit ensures that the performance of the augmented prosthesis component is not compromised. Moreover, the augmentation system of the invention can be easily attached within a femoral component of a knee joint prosthesis. Of particular significance is the fact that the augmentation system of the invention can be used in both left and right side joint prostheses, and in various areas of joint prostheses without modification. The augmentation system of this invention also offers the advantage that the collet can secure the augmenting block to a prosthesis by securely engaging a mounting cavity within the prosthesis having an as cast tolerance.

The foregoing description of the illustrative embodiment of the invention is presented to indicate the range of constructions to which the invention applies. Variations in the physical architecture and dimensions of the augmentation system will be apparent to those having ordinary skill in the art based upon the disclosure herein, and such variations are considered to be within the scope of the invention in which patent rights are asserted, as set forth in the claims appended hereto. All publications and references cited herein are expressly incorporated herein by reference in their entirety.

What is claimed is:

1. An augmentation system for an artificial knee prosthesis, comprising:

a femoral component having an articulation surface and an opposed, bone engaging surface, the bone engaging surface having at least one mounting cavity disposed in a portion thereof;

an augmenting block, mountable on a portion of the bone engaging surface of the femoral component, the augmenting block having first and second opposed surfaces, an aperture extending between the first and second surfaces, and a recessed area formed around the aperture in the second surface of the augmenting block;

an expansion collet matable entirely within the aperture such that a stem at a distal end thereof extends beyond a first surface of the augmenting block, the stem having a diameter that is adjustable between a contracted condition in which the stem non-engagingly fits within the cavity of the femoral component in an expanded condition in which the stem engages the walls of the mounting cavity to secure the augmenting block to the femoral component;

an internal, threaded cavity formed within a proximal end of the expansion collet; and a set screw element having external threads at a proximal end thereof, fixedly mountable entirely within the proximal end of the internal, threaded cavity of the expansion collet, that is effective to adjust the diameter of the stem between the contracted and expanded conditions to secure the augmenting block to the bone engaging surface of the femoral component.

2. The device of claim 1 wherein the collet is frictionally and/or mechanically engaged within the aperture.

3. The device of claim 2 wherein a recessed area of a second surface of the block surrounds the aperture of the augmenting block.

4. The device of claim 3 wherein the proximal end of the collet includes a collar that seats within the recessed area of the augmenting block.

5. The device of claim 4 wherein the collar is D-shaped.

6. The device of claim 4 wherein the collar is round.

7. The device of claim 1 wherein the cavity of the collet has a slotted and dogged distal end.

8. The device of claim 1 wherein the mounting cavity is substantially round.

9. The device of claim 1 wherein a distal end of the set screw means includes an angular dog point or radius tip.

10. The device of claim 1 wherein the stem at the distal end of the collet has a diameter ranging from about 0.240 to 0.260 inch in the contracted condition to about 0.250 to 0.270 inch in the expanded condition.

11. The augmentation system of claim 1, wherein the femoral component includes a raised surface feature on the bone engaging surface and wherein the augmenting block further comprises a recesses formed in the first surface of the augmenting block that is engagable with the raised surface feature.

* * * * *